(12) United States Patent
Shimojo et al.

(10) Patent No.: US 7,553,946 B2
(45) Date of Patent: Jun. 30, 2009

(54) PROMOTERS

(75) Inventors: Tomoko Shimojo, Kyoto (JP); Hikaru Takakura, Shiga (JP); Kazuyori Ochiai, Shiga (JP); Kiyozo Asada, Shiga (JP); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 232 days.

(21) Appl. No.: 11/500,480

(22) Filed: Aug. 8, 2006

(65) Prior Publication Data

US 2006/0269999 A1    Nov. 30, 2006

Related U.S. Application Data

(62) Division of application No. 10/471,868, filed as application No. PCT/JP02/02341 on Mar. 13, 2002, now Pat. No. 7,125,690.

(30) Foreign Application Priority Data

Mar. 14, 2001    (JP)    ............................ 2001-072802

(51) Int. Cl.
*C12N 15/11*    (2006.01)
*C12N 15/00*    (2006.01)
*C12N 15/63*    (2006.01)

(52) U.S. Cl. .................. 536/23.1; 435/69.1; 435/320.1

(58) Field of Classification Search .................. None
See application file for complete search history.

(56) References Cited

OTHER PUBLICATIONS

Tosato et al., Sequence completion, identification and definition of the fengycin operon in *Bacillus subtilis* 168, *Microbiology*, 143:3443,3450 (1997).
Database EMBL, *Bacillus subtilis*, retrieved from EBI Database, Accession No. L04519, XP-002291831, Oct. 28, 1992.
Database EMBL, *Bacillus subtilis*, retrieved from EBI Database, Accession No. Y15896, XP-002291833, Feb. 11, 2000.
Duitman, Erwin H. et al., "The mycosubtilin synthetase of *Bacillus subtilis* ATCC6633: A multifunctional hybrid between a peptide synthetase, an amino transferase, and a fatty acid synthase", Proceedings of the National Academy Sciences, vol. 96, No. 23, pp. 13294-13299, Nov. 9, 1999.
Database EMBL, *Bacillus subtilis*, retrieved from EBI Database, Accession No. AF184956, XP-002291869, Nov. 18, 1999.
Mohan, Sandhya et al., "Molecular Cloning and Characterization of comC, a Late Competence Gene of *Bacillus subtilis*", Journal of Bacteriology, vol. 171, No. 11, pp. 6043-6051, Nov. 1989.
Database EBML, *Bacillus subtilis*, retrieved from EBI Database, Accession No. M30805, XP-002291832, Apr. 19, 1990.
Ray, C. et al., "Mutations That Affect Utilization of a Promoter in Stationary-Phase *Bacillus subtilis*", Journal of Bacteriology, Aug. 1985, vol. 163, No. 2, pp. 610-614.
Huang, M. et al, entitled "Biochemical and molecular characterization of the *Bacillus subtilis* acetoin catabolic pathway", Database EMBL 'Online! retrieved from EBI, Database accession No. AF006075, XP0022855992, abstract.
Min Huang et al, "Biochemical and Molecular Chatacterization of the *Bacillus subtilis* Acetoin Catabolic Pathway", Journal of Bacteriology, Apr. 5, 1999, vol. 181, No. 12, pp. 3837 to 3841.
F. Kunst et al, "The Complete Genome Sequence of the Gram-Positive Bacterium *Bacillus subtilis*", Nature, Nov. 20, 1997, vol. 390, No. 6657, pp. 249 to 256.
Peter S. Margolis et al, "Sporulation Gene SPOIIB From *Bacillus subtilis*", journal of bacteriology, Jan. 1993, vol. 175, No. 2, pp. 528 to 540.
Valentina Tosato et al, "Sequence Completion, Identification and Definition of the Fengycin Operon in *Bacillus subtilis* 168", Microbiology, 1997, vol. 91, pp. 162.
D.L. Frisby et al, "Mulational Analysis of a Stationary Phase-Induced Promoter in *Bacillus subtilis*", Abstracts of the General meeting of the American Society for Microbiology, 1991, vol. 91, pp. 162.
Database EMBL, Accession No. DI010959, XP-002496171.

*Primary Examiner*—Nancy Vogel
*Assistant Examiner*—Michele K. Joike
(74) *Attorney, Agent, or Firm*—Browdy and Neimark, PLLC

(57)    ABSTRACT

Isolated DNAs which are DNAs having a base sequence represented by any of SEQ ID NOS:1 to 6 in Sequence Listing or fragments thereof and showing a stationary phase-specific promoter activity in gram positive bacteria.

7 Claims, No Drawings

US 7,553,946 B2

PROMOTERS

CROSS-REFERENCE TO RELATED APPLICATIONS

The present application is a division of Ser. No. 10/471,868, which is a 371 national stage application of PCT/JP01/02341, filed Mar. 13, 2002. The entire contents of both applications are incorporated herein by reference.

TECHNICAL FIELD

The present invention relates to a novel promoter capable of expressing a gene product of interest conveniently, at a low cost and at a high level, and a method for producing a protein using the promoter.

BACKGROUND ART

Expression systems are utilized for producing useful gene products by genetic engineering depending on the purposes. In the expression systems, hosts for which techniques for their cultivation have been established such as microbial cells (*Escherichia coli, Bacillus subtilis*, yeast, etc.), animal cells, insect cells and plant cells, and promoters suitable for the hosts are used. Among these, an expression system in which *Escherichia coli* as a host and the lac promoter or a derivative thereof are used is one of the most commonly used systems because of the operational convenience.

However, the expression system in which the lac promoter or a derivative thereof is used has a drawback in that it is industrially disadvantageous because it requires induction of gene expression for expression of a gene product. For example, induction of gene expression from the lac promoter, the tac promoter or the like requires use of an expensive reagent, isopropyl-β-D-thiogalactopyranoside (IPTG). Therefore, such a system has a drawback in that it is disadvantageous to performance on an industrial scale.

An expression system in which a promoter derived from xylose operon and a bacterium of the genus *Bacillus* as a host are utilized is also used. However, the system is disadvantageous to performance on an industrial scale because it requires addition of xylose for the expression induction.

Expression vectors that utilize thermoinduction of the phage λ promoter are generally used.

However, overexpression of recombinant gene products by thermoinduction may be disadvantageous in the following points:

(a) difficulty in rapidly achieving shifting-up of a temperature;

(b) increased possibility of forming insoluble inclusion bodies due to a higher cultivation temperature; and (c) induction of several proteases in *Escherichia coli* upon heat shock.

*Bacillus subtilis* is known to produce and secrete a number of catabolic enzymes such as amylases and proteases as a result of a stationary phase-specific response. If one could express a gene only during stationary phase after full growth of a host utilizing the stationary phase-specific expression mechanism, the burden on the host might be decreased, and an exogenous gene might be efficiently expressed. However, no gene expression technique in which such a mechanism is utilized has been established.

Thus, a technique that enables efficient expression without artificially inducing gene expression has been desired.

OBJECTS OF INVENTION

The main, object of the present invention is to provide a promoter, a recombinant DNA, a vector for expressing a gene, an expression vector and a transformed cell that enable expression of a gene at a high level in a stationary phase-specific manner without artificially inducing the expression of the gene, as well as a method for producing a protein which can be carried out conveniently and at a low cost, and a kit for the method.

SUMMARY OF INVENTION

The present invention is outlined as follows:

[1] an isolated DNA selected from the group consisting of:

(a) an isolated DNA having a nucleotide sequence of any one of SEQ ID NOS:1 to 6 or a fragment thereof which exhibits a promoter activity in a Gram-positive bacterium in a stationary phase-specific manner; and (b) an isolated DNA hybridizable to the DNA or a fragment thereof of (a) under stringent conditions which exhibits a promoter activity in a Gram-positive bacterium in a stationary phase-specific manner;

[2] the isolated DNA according to [1], which is capable of expressing an exogenous gene in a stationary phase-specific manner in the absence of an inducer when the DNA is placed upstream of the gene;

[3] a recombinant DNA in which the DNA defined by [1] and an exogenous gene are placed such that the exogenous gene can be expressed;

[4] the recombinant DNA according to [3], wherein the exogenous gene is a nucleic acid selected from the group consisting of nucleic acids encoding proteins, nucleic acids encoding antisense RNAs and nucleic acids encoding ribozymes;

[5] a vector for expressing a gene which contains the DNA defined by [1];

[6] the vector for expressing a gene according to [5], wherein the vector is one selected from the group consisting of plasmid vectors, phage vectors and virus vectors;

[7] an expression vector which contains the recombinant DNA defined by [3];

[8] the expression vector according to [7], wherein the vector is one selected from the group consisting of plasmid vectors, phage vectors and virus vectors;

[9] a transformed cell which harbors the recombinant DNA defined by [3] or the expression vector defined by [7];

[10] a method for producing a protein, the method comprising:

culturing the transformed cell defined by [9]; and collecting a protein from the resulting culture; and

[11] a kit for producing a protein which contains the DNA defined by [1] or the vector for expressing a gene defined by [5].

DETAILED DESCRIPTION OF THE INVENTION

A DNA derived from *Bacillus subtilis* DB104 (Gene, 83:215-233 (1989)) containing an element that is located upstream of an open reading frame (ORF) for a gene expressed in a stationary phase-specific manner, and exhibits an promoter activity can be used as the DNA of the present invention. The present invention is based on the surprising finding by the present inventors that if an exogenous gene (also referred to as a gene of interest) is placed downstream of the DNA, the gene product of interest can be expressed at a high level, i.e., 100 to 500 mg per liter of a medium, in the absence of an expression inducer.

The DNAs of the present invention include DNAs having nucleotide sequences of SEQ ID NOS:1 to 6. The DNA of the present invention is preferably an isolated DNA that exhibits a promoter activity in a stationary phase-specific manner in a Gram-positive bacterium, more preferably an isolated DNA that exhibits a promoter activity in a stationary phase-specific manner in a bacterium of the genus *Bacillus* or *Escherichia coli* as described below.

According to the present invention, "a promoter" comprises a Pribnow box, a TATA box or a region similar to the TATA box which is located about 10 to 30 base pairs upstream from a transcription initiation site (+1) and is responsible for a function of allowing an RNA polymerase to initiate transcription from an exact position. The promoter is not necessarily restricted to such a region or surrounding regions, but may comprise, in addition to the region, a region necessary for association of a protein other than an RNA polymerase for controlling expression. As used herein, the term "a promoter region" refers to a region containing the promoter according to the present invention.

As used herein, "a promoter activity" means that when a construct, which is obtained by placing a gene downstream of a promoter such that the gene can be expressed, is introduced into a host, the promoter functions to enable the production of an expression product from the gene inside or outside the host.

Generally, "a promoter activity" can be measured using a process comprising:

(1) a step of connecting a DNA to be subjected to measurement to upstream of a gene encoding a protein that can be readily quantified or observed (hereinafter also referred to as a reporter gene);

(2) a step of introducing the resulting construct into a host;

(3) a step of culturing the resulting transformed cell to express the protein; and (4) a step of measuring the amount of the expressed protein. For example, the presence of "a promoter activity" can be determined by connecting a sequence that is presumed to have a promoter sequence to upstream of a reporter gene, introducing the construct into a host, and observing the expression of the gene product inside or outside the host. The observation of expression serves as an index of the promoter activity of the promoter in the introduced host.

As used herein, "a stationary phase-specific promoter" refers to a promoter that directs transcription only during stationary phase after logarithmic growth phase. "A stationary phase-specific promoter" can express a gene placed downstream of the promoter only during stationary phase without induction using an inducer such as IPTG.

The DNAs of the present invention include fragments of the isolated DNAs having nucleotide sequences of SEQ ID NOS:1 to 6 as long as the fragments exhibit promoter activities in a stationary phase-specific manner. "A fragment" can be appropriately selected such that it exhibits a promoter activity in a stationary phase-specific manner. Such a fragment can be selected using the above-mentioned process comprising the steps (1) to (4).

The DNAs of the present invention further include a DNA that has a nucleotide sequence in which at least one nucleotide, specifically one or several nucleotides are substituted, deleted, inserted or added in any one of the nucleotide sequences of SEQ ID NOS:1 to 6, and has a promoter activity in a stationary phase-specific manner. In general, the activity of a DNA having a short sequence may be altered if it has a mutation (substitution, deletion, insertion or addition) of at least one nucleotide. However, "a DNA having a mutation" is encompassed by the present invention if a promoter activity is observed for the DNA in a stationary phase-specific manner using the above-mentioned process comprising the steps (1) to (4). The mutation may be either a naturally occurring or artificially introduced mutation.

An artificial mutation can be introduced according a conventional site-directed mutagenesis method or the like. Examples of the site-directed mutagenesis methods that can be used include the gapped duplex method which utilizes an amber mutation (Nucleic Acids Research, 12:9441-9456 (1984); the Kunkel method in which a host deficient in the dut (dUTPase) and ung (uracil-DNA glycosylase) genes is utilized (Proceedings of the National Academy of Sciences of the USA, 82:488-492 (1985)) and a PCR method utilizing an amber mutation (WO 98/02535).

The present invention also encompasses an isolated DNA that is hybridizable to the complementary strand of the DNA of the present invention under stringent conditions or, for example, obtained using an oligonucleotide probe or primer that is designed and chemically synthesized according to conventional methods based on the DNA of the present invention, and that has a promoter activity in a stationary phase-specific manner, preferably in a Gram-positive bacterium.

For example, a DNA for which a promoter activity is observed in a stationary phase-specific manner using the above-mentioned process comprising steps (1) to (4) may be selected as such a DNA. There is no specific limitation concerning the nucleotide sequence of the oligonucleotide probe as long as the oligonucleotide probe hybridizes to the DNA or a DNA having a nucleotide sequence complementary to the DNA under stringent conditions.

"Stringent conditions" are exemplified by those as described in a literature such as Sambrook et al., Molecular cloning, A laboratory manual $2^{nd}$ edition, 1989, Cold Spring Harbor Laboratory Press. For example, the stringent conditions are incubation at a temperature of [Tm of the probe to be used −25° C.] overnight in a solution containing 6×SSC (1×SSC: 0.15 M NaCl, 0.015 M sodium citrate, pH 7.0) 0.5% SDS, 5× Denhardt's (0.1% bovine serum albumin (BSA), 0.1% polyvinylpyrrolidone, 0.1% Ficoll 400) and 100 µg/ml of salmon sperm DNA.

There is also no specific limitation concerning the nucleotide sequence of the primer as long as the primer can anneal to the DNA or a DNA having a nucleotide sequence complementary to the DNA to initiate an extension reaction with a DNA polymerase under conditions used for a conventional PCR.

Tm of an oligonucleotide probe or primer can be determined, for example, according to the following equation:

$$Tm=81.5-16.6(\log_{10}[Na^+])+0.41(\%G+C)-(600/N)$$

wherein N is the chain length of the oligonucleotide probe or primer; %G+C is the content of guanine and cytosine residues in the oligonucleotide probe or primer.

If the chain length of the oligonucleotide probe or primer is shorter than 18 nucleotides, Tm can be estimated, for example, as the sum of the product of the number of A+T (adenine and thymine) residues multiplied by 2(° C.) and the product of the number of G+C residues multiplied by 4(° C.), i.e., [(A+T)×2+(G+C)×4].

Although it is not intended to limit the present invention, it is desirable that the chain length of the oligonucleotide probe or primer is preferably 6 nucleotides or more, more preferably 10 nucleotides or more in order to avoid nonspecific hybridization or annealing. Furthermore, it is desirable that the length is preferably 100 nucleotides or less, more preferably 30 nucleotide or less in view of synthesis of the oligonucleotide.

Designing of an oligonucleotide is known to those skilled in the art and can be carried out, for example, with reference to Labo Manual PCR, pp. 13-16, 1996 (Takara Shuzo). Alternatively, a commercially available software such as OLIGO™ Primer Analysis software (Takara Shuzo) may be used.

The oligonucleotide can be synthesized according to a known method. For example, it can be synthesized using a DNA synthesizer Model 394 (Applied Biosystems) according to the phosphoramidite method. Alternatively, the phosphate triester method, the H-phosphonate method, the thiophosphonate method or the like may be used for the synthesis.

Using the DNA of the present invention, a recombinant DNA in which the DNA and an exogenous gene are placed such that the exogenous gene can be expressed is provided. Such a recombinant DNA is encompassed by the present invention.

Examples of the exogenous genes include, but are not limited to, nucleic acids encoding proteins (e.g., enzymes, cytokines or antibodies), nucleic acids encoding antisense RNAs and nucleic acids encoding ribozymes. Examples of the origins of the exogenous genes include, but are not limited to, microorganisms (e.g., bacteria, yeasts, actinomycetes, filamentous fungi, ascomycetes and basidiomycetes); plants; insects; and animals. Furthermore, artificially synthesized genes may be used depending on the purpose.

Specifically, examples of the exogenous genes include, but are not limited to, the interleukin (IL) 1 to 12 genes, the interferon (IFN) $\alpha$, $\beta$ and $\gamma$ genes, the tumor necrosis factor (TNF) gene, the colony-stimulating factor (CSF) genes, the erythropoietin gene, the transforming growth factor (TGF)-$\beta$ gene, the immunoglobulin (Ig) gene, the tissue plasminogen activator (t-PA) gene, the urokinase gene and the Western firefly luciferase gene.

As used herein, "a ribozyme" refers to one that cleaves an mRNA for a specific protein to inhibit the translation of the protein. A ribozyme can be designed on the basis of a sequence of a gene encoding a specific protein. For example, a hammerhead ribozyme can be prepared using the method as described in FEBS Letter, 228:228-230 (1988). The ribozymes according to the present invention include any one that cleaves an mRNA for a specific protein to inhibit the translation of the protein regardless of the type of the ribozyme (e.g., hammerhead, hairpin or delta).

The DNA of the present invention exhibits a promoter activity that enables expression of a gene at a high level even if the gene expression is not artificially induced. Therefore, it is particularly preferable for expression of an exogenous gene which is a nucleic acid encoding a protein.

Furthermore, using the DNA of the present invention, a vector for expressing a gene that contains the DNA is provided. Such a vector for expressing a gene is encompassed by the present invention.

It is possible to express a protein as an example of gene products of interest at a level of 100 to 500 mg per liter of a medium using the vector for expressing a gene of the present invention because it contains the DNA of the present invention. A gene product of interest can be readily expressed depending on the intended use.

A plasmid vector, a phage vector or a virus vector, or a vector fragment consisting of a portion of the vector may be used as a vector in the vector for expressing a gene of the present invention. The vector or the vector fragment can be appropriately selected depending on the cell to be use as a host.

There is no specific limitation concerning the cell that can be used as a host. For example, a Gram-positive bacterium may be used. Examples of the Gram-positive bacteria include bacteria of the genus *Bacillus* for which transformation systems have been established. Specifically, *Bacillus subtilis*, *Bacillus stearothermophilus*, *Bacillus licheniformis*, *Bacillus brevis* or *Bacillus* sp. may be used, although it is not intended to limit the present invention. One obtained by mutagenizing such a bacterium of the genus *Bacillus* may be used as a host. Also, *Escherichia coli* may be used as a host. Transformation systems for *Escherichia coli* have been established, *Escherichia coli* cells with various genotypes have been created, and they are readily available. Therefore, *Escherichia coli* is widely used as a host for transformation. Specific examples include strains HB101, C600, JM109, DH5α, DH10B, XL-1BlueMRF' and TOP10F derived from *Escherichia coli* K-12, although it is not intended to limit the present invention. One obtained by mutagenizing such an Escherichia coli cell may be used as a host.

If a bacterium of the genus *Bacillus* is used as a host, examples of the vectors include plasmid vectors such as pHY, pUB110 and pE194 as well as phage vectors such as φ105 and SPβ. If Escherichia coli is used as a host, examples of the vectors include plasmid vectors such as pUC18, pUC19, pBluescript and pET as well as phage vectors such as lambda phage vectors (e.g., λgt10 and λgt11). The vector for expressing a gene of the present invention which is capable of expressing an exogenous gene in a stationary phase-specific manner can be constructed by appropriately selecting such a vector and incorporating the DNA of the present invention into it.

Techniques as described in Molecular cloning, A laboratory manual $2^{nd}$ edition (supra) or the like can be utilized for the construction of the vector for expressing a gene of the present invention. Alternatively, the construction may be carried out according to the construction procedures as described in Examples below, for example.

The vector for expressing a gene of the present invention may contain a terminator (e.g., rrnBT1T), a selectable marker gene and the like.

Selectable marker genes include the ampicillin-resistance gene, the kanamycin-resistance gene, the chloramphenicol-resistance gene and the tetracyclin-resistance gene.

The vector for expressing a gene of the present invention may contain the following depending on the intended use of the gene product of interest. For example, it may contain, in order to simplify the procedure for isolating the gene product of interest, a sequence that enables expression as a fusion protein with a heterologous protein (e.g., glutathione S-transferase or maltose-binding protein), or a tag sequence that enables expression as a protein to which a histidine tag or the like is added.

Furthermore, the present invention provides an expression vector that contains the above-mentioned recombinant DNA. Such an expression vector is encompassed by the present invention. The expression vectors of the present invention include a construct obtained by incorporating a gene of interest into the above-mentioned vector for expressing a gene.

The vector as described above with respect to the vector for expressing a gene can be used for the expression vector of the present invention.

The expression vector of the present invention can be constructed by (a) incorporating the recombinant DNA into an appropriate vector; (b) incorporating a gene of interest into the vector for expressing a gene; or (c) connecting a gene of interest to the vector fragment for expressing a gene.

Using the recombinant DNA or the expression vector of the present invention, a transformed cell that harbors the recombinant DNA or the expression vector can be also provided.

"The cell that can be used as a host" as described above may be used as a host.

For example, a recombinant DNA can be introduced into a host according to the method as described in Idenshikougaku Jikken, pp. 12-23, Japan Radioisotope Association (ed.) (1991); Virology, 52:456 (1973); Molecular and Cellular Biology, 7:2745 (1987); Journal of the National Cancer Institute, 41:351 (1968); or EMBO Journal, 1:841 (1982).

For example, an expression vector can be introduced into a host according to the spontaneous competence method (Idenshikougaku Jikken, pp. 12-23, Japan Radioisotope Association (ed.) (1991)); the calcium phosphate method (Molecular and Cellular Biology, 7:2745 (1987)); the electroporation method (Proc. Natl. Acad. Sci. USA, 81:7161 (1984)); the DEAE-dextran method (Methods in Nucleic Acids Research, pp. 283, Karam et al. (eds.) (1991) CRC Press); or the liposome method (BioTechniques, 6:682 (1989)).

Using the transformed cell of the present invention, a method for producing a protein comprising culturing the transformed cell, and collecting a protein from the resulting culture is provided. Such "a method for producing a protein" is encompassed by the present invention.

Specifically, a protein can be produced by a method comprising:

(I) a step of transforming a host cell with:

(a) a recombinant DNA in which a nucleic acid encoding a protein is placed downstream of the DNA of the present invention such that the nucleic acid can be expressed; or (b) a vector containing the recombinant DNA; and (II) a step of culturing the transformed cell obtained in (I) and collecting the protein from the resulting culture.

A method for culturing the transformed cell can be appropriately selected depending on the cell to be used as a host, the property of the protein to be expressed and the like.

The thus obtained protein can be purified by a conventional means of purifying a protein. Examples of such purification means include salting out, ion exchange chromatography, hydrophobic chromatography, affinity chromatography and gel filtration chromatography.

A kit for producing a protein that contains the DNA of the present invention or the vector for expressing a gene of the present invention can be constructed and used for the method for producing a protein of the present invention. Using such a kit, a protein can be produced more conveniently.

EXAMPLES

The following Examples illustrate the present invention in more detail, but are not to be construed to limit the scope thereof.

Relationship between and properties of *Bacillus subtilis* strains used according to the present invention are described below.

*B. subtilis* Marburg 168: the parent strain of strains generally used as *Bacillus subtilis* hosts in recombinant DNA experiments.

*B. subtilis* DB104: one of derivatives of *B. subtilis* Marburg 168 which requires histidine. Mutations other than the auxotrophy (nprR2, nprE18, aprED3) are identical to those of UOT1285.

*B. subtilis* UOT1285: one of derivatives of *B. subtilis* Marburg 168 which requires tryptophan and lysine. Mutations other than the auxotrophies (nprR2, nprE18, aprED3) are identical to those of DB104.

Example 1

Screening of Genes Expressed in a Stationary Phase-Specific Manner Using a *Bacillus subtilis* DNA Chip PCR primers were designed using the DNA sequence information in the *Bacillus subtilis* genome database (genolist.pasteur.fr/SubtiList/genome.cgi) such that almost full-length ORFs can be amplified for all the ORFs of *Bacillus subtilis*. PCRs were carried out using these primers, a genomic DNA from *Bacillus subtilis* Marburg 168 (Molecular & General Genetics, 152:65-69 (1977)) and TaKaRa Ex Taq (Takara Shuzo) or TaKaRa Z-Taq (Takara Shuzo) in a 96-well plate.

The resulting PCR products were purified. The purity and the size were checked by agarose gel electrophoresis, and the DNA concentration was then calculated by measuring the absorbance for each one.

The thus obtained DNA fragment solutions were concentrated by isopropanol precipitation. DNA fragments each at a concentration of 1.0 μg/ml were immobilized onto a slide glass according to the method as described in WO 00/26404 to prepare a DNA chip.

*Bacillus subtilis* UOT1285 (Journal of General Microbiology, 135:1335-1345 (1989)) was cultured in 50 ml of 2×SG (1.6% Nutrient Broth, 0.05% $MgSO_4.7H_2O$, 0.2% KCl, 1 mM $Ca(NO_3)_2.4H_2O$, 0.1 mM $MnCl_2.4H_2O$, 0.001 mM $FeSO_4.7H_2O$, 0.1% glucose) at 37° C. A portion of the culture was taken 3, 4 or 5 hours after the initiation of cultivation, and cells were collected by centrifugation. The thus obtained cells were suspended in TRIZOL Reagent (Gibco BRL). Glass beads were added thereto. The cells were disrupted using Mini-BeadBeater (Biospec Products). An RNA was recovered by chloroform extraction and isopropanol precipitation according to the protocol attached to TRIZOL Reagent. The recovered RNA was treated with RNase-free DNase I (Takara Shuzo), and then recovered by phenol/chloroform extraction followed by ethanol precipitation. As a result, about 90-100 μg of RNA was obtained. The RNA was used as an RNA as a template.

A reverse transcriptase reaction was carried out using 15 μg of the RNA as a template prepared as described above and Cy3-dUTP (Amersham Pharmacia Biotech) to prepare a Cy3-labeled cDNA probe.

The DNA chip prepared as described above was subjected to prehybridization in a prehybridization solution (4×SSC, 0.2% SDS, 5× Denhardt's solution, 1 mg/ml of denatured salmon sperm DNA) at room temperature for 2 hours, washed in 2×SSC followed by 0.2×SSC, and then dried. Then, hybridization was carried out at 65° C. overnight using the Cy3-labeled cDNA probe prepared as described above in a hybridization solution which had the same composition as the prehybridization solution except that the concentration of the denatured salmon sperm DNA was changed to 0.1 mg/ml. After hybridization, the DNA chip was washed in 2×SSC containing 0.2% SDS at 55° C. for 30 minutes (twice) and at 65° C. for 5 minutes (once), and in 0.05×SSC at room temperature for 5 minutes, and then dried.

The hybridized DNA chip was subjected to fluorescence detection using a DNA chip analysis apparatus Affymetrix 418 Array Scanner (Affymetrix). The signal intensities obtained by the fluorescence detection are expressed as color ranks in an image as follows: blue<green<yellow<orange<red<white.

The thus obtained image data were subjected to measurements and analyses of signal intensities using an expression data analysis software ImaGene (BioDiscovery) according to the instructions attached to the software. The values of numerically expressed Cy3 signal intensities corrected using the signal for rRNA as an internal standard were compared, and expression signals for genes at respective growth stages of *Bacillus subtilis* were determined. As a result, there were genes for which strong expression signals were observed after 3 hours of cultivation, genes for which strong expression signals were observed after 5 hours of cultivation, and the like. Thus, it was shown that the expression patterns of the ORFs were clearly different from each other.

The growth stage-specificity of expression level was determined by calculating a ratio of relative expression level by dividing the expression signal after 4 or 5 hours of cultivation by the expression signal after 3 hours of cultivation in order to examine the difference in expression signals in more detail. Results for representative genes are shown in Table 1.

TABLE 1

| Gene | Signal ratio (4 hours/3 hours) | Signal ratio (5 hours/3 hours) |
|---|---|---|
| iolJ | 4.37 | 30.5 |
| sigF | 1.17 | 80.3 |
| sipW | 0.63 | 10.9 |
| spoIIB | 2.21 | 26.5 |
| spoIIIAH | 0.55 | 10.7 |
| spoIVA | 1.30 | 26.4 |
| yabS | 1.93 | 42.8 |
| ybcO | 1.15 | 18.0 |
| ybcP | 1.86 | 34.6 |
| ybcQ | 1.89 | 33.1 |
| ybcS | 1.30 | 27.5 |
| ybcT | 1.35 | 23.2 |
| ybdA | 1.17 | 14.3 |
| yjdB | 3.11 | 31.4 |
| yngJ | 1.03 | 6.54 |
| yobH | 2.80 | 4.15 |
| yqxA | 0.10 | 31.2 |
| yrzE | 2.46 | 38.4 |

As seen from Table 1, there were genes for which expression levels were remarkably increased after 5 hours of cultivation, i.e., during stationary phase.

Example 2

Screening of Genes Expressed in a Stationary Phase-Specific Manner using a *Bacillus subtilis* Macromembrane A digoxigenin (hereinafter referred to as DIG)-labeled cDNA probe was prepared by carrying out a reverse transcriptase reaction using 15 μg of the RNA as a template prepared in Example 1 and DIG-11-dUTP (Roche Diagnostics).

Next, hybridization to *Bacillus subtilis* DNA array (Eurogentec; hereinafter referred to as a macromembrane; putative ORFs derived from *B. subtilis* Marburg 168) was carried out using the DIG-labeled cDNA probe. For hybridization, prehybridization was carried out in a solution of DIG Easy Hyb Granules (Roche Diagnostics) at 42° C. for 30 minutes, and hybridization was then carried out at 42° C. overnight. Detection was carried out using DIG Wash and Block Buffer and Detection kit (both from Roche Diagnostics).

The detection results were developed on a photosensitive film. The image was taken into an image analysis apparatus Model GS-700 Imaging Densitometer (Bio-Rad) using an image analysis software Adobe Photoshop (Adobe). The signal intensities were measured and analyzed using an image analysis software MultiAnalyst (Bio-Rad) according to the instructions attached to the software. Expression signals for genes at respective growth stages of *Bacillus subtilis* were measured on the basis of numerically expressed DIG signal intensities. As a result, there were genes for which strong expression signals were observed after 3 hours of cultivation, genes for which strong expression signals were observed after 5 hours of cultivation, and the like. Thus, it was shown that the expression patterns of the ORFs were clearly different from each other.

The growth stage-specificity of expression level was determined by calculating a ratio of relative expression level by dividing the expression signal after 4 or 5 hours of cultivation by the expression signal after 3 hours of cultivation in order to examine the difference in expression signals in more detail. Results for representative genes are shown in Table 2.

TABLE 2

| Gene | Signal ratio (4 hours/3 hours) | Signal ratio (5 hours/3 hours) |
|---|---|---|
| acoA | 4.42 | 42.8 |
| acoL | 7.17 | 68.2 |
| sigF | 0.79 | 8.18 |
| sipW | 8.16 | 26.3 |
| spoIIB | 2.78 | 11.6 |
| spoIVA | 2.15 | 3.35 |
| yabS | 0.80 | 10.9 |
| ybcO | 3.45 | 14.5 |
| ybcP | 6.86 | 31.8 |
| ybcQ | 1.41 | 51.0 |
| ybcS | 6.39 | 53.1 |
| ybcT | 3.13 | 22.2 |
| ybdA | 1.81 | 8.95 |
| ybdD | 0.20 | 18.8 |
| yfiA | 0.55 | 5.21 |
| ygaB | 0.16 | 1.65 |
| yjdB | 4.18 | 14.4 |

As seen from Table 2, there were genes for which expression levels were remarkably increased after 5 hours of cultivation, i.e., during stationary phase.

Example 3

Screening of Stationary Phase-Specific Promoters

For screening of stationary phase-specific promoters, two rounds of the respective screenings as described in Examples 1 and 2 were carried out, genes for which expression levels were remarkably increased after 5 hours of cultivation, i.e., during stationary phase were totally judged on the basis of the results, and the following 23 genes were selected and used for experiments below: acoA, acoL, iolJ, sigF, sipw, spoIIB, spoIIIAH, spoIVA, yabs, ybcO, ybcp, ybcQ, ybcS, ybcT, ybda, ybdD, yfiA, ygaB, yjdB, yngJ, yobH, yqxA and yrzE.

Screening of stationary phase-specific promoters was carried out by connecting an exogenous gene to DNA fragments from the 23 genes expressed in a stationary phase-specific manner that were presumed to contain promoter regions for the genes to construct vectors for expressing the exogenous gene.

Commercially available enzymes for gel purification and plasmid purification and kits for gel purification and plasmid purification were used for constructing the vectors for expressing the gene. Unless otherwise noted, procedures were carried out according to the methods as described in Molecular cloning, A laboratory manual $2^{nd}$ edition (Sambrook et al., 1989, Cold Spring Harbor Laboratory Press).

A total of 46 primers were designed for amplifying about 180-bp DNA fragments containing upstream regions of the 23 genes expressed in a stationary phase-specific manner. The regions in the DNA fragments were located upstream from the SD sequences for the genes and presumed to contain promoters. The designing was carried out on the basis of the sequences in the *Bacillus subtilis* genome database as described in Example 1 (genolist.pasteur.fr/SubtiList/genome.cgi). In addition, sites for restriction enzymes KpnI and EcoRI were added on both sides of the respective designed primers in order to simplify the procedures following amplification.

The genes from which the DNA fragments presumed to contain promoter regions were to be amplified, the primers used for amplification, and SEQ ID NOS showing the sequences of the primers (in parentheses) are as follows: the acoA gene, primers aAF1 (SEQ ID NO:7) and aAR1 (SEQ ID NO:8); the spoIIB gene, primers spBF1 (SEQ ID NO:9) and spBR1 (SEQ ID NO:10); the ybco gene, primers ybOF1 (SEQ ID NO:11) and ybOR1 (SEQ ID NO:12); the yjdB gene, primers yjBF1 (SEQ ID NO:13) and pjBR1 (SEQ ID NO:14); the yngJ gene, primers ynJF1 (SEQ ID NO:15) and ynJR1 (SEQ ID NO:16); and the yrzE gene, primers yrEF1 (SEQ ID NO:17) and yrER1 (SEQ ID NO:18).

A genomic DNA was prepared from *Bacillus subtilis* DB104 (Gene, 83:215-233 (1989)) using ISOPLANT kit (Nippon Gene) according to the instructions attached to the kit.

A PCR was carried out using the genomic DNA as a template and the primers designed as described above as follows: 20 cycles of 94° C. for 30 seconds, 50° C. for 1 minute, and 72° C. for 1 minute.

The 23 DNA fragments presumed to contain promoters which were amplified as described above were used below.

A gene for a hyperthormostable protease PFUS derived from *Pyrococcus furiosus* as described in WO 98/56926 was used as an exogenous gene to be used for screening stationary phase-specific promoters.

*Bacillus subtilis* DB104/pSPO124ΔC (FERM BP-6294) is a strain that harbors a plasmid pSPO124ΔC containing the hyperthermostable protease PFUS gene as described in WO 98/56926. *Bacillus subtilis* DB104/pSPO124ΔC was cultured in 5 ml of LB medium containing 10 µg/ml of kanamycin at 37° C. overnight. The plasmid pSPO124ΔC was then prepared from collected cells using QIAGEN Plasmid Mini kit (Qiagen) according to the instructions attached to the kit. In this case, cells suspended in the buffer P1 attached to the kit to which lysozyme was added at a concentration of 4 mg/ml were treated at 37° C. for 30 minutes.

A 5448-bp DNA fragment was amplified by a PCR using the plasmid pSPO0124ΔC as a template and primers PLF1 (SEQ ID NO:19) and PLR1 (SEQ ID NO:20). The fragment contained the SD sequence and the secretion signal of the aprE gene which encodes subtilisin E from *Bacillus subtilis*, as well as the structural gene for the hyperthermostable protease PFUS. This fragment was used as a vector fragment below.

Procedures are described below with respect to a DNA fragment containing a promoter region for the yngL gene as an example.

The amplified DNA fragment presumed to contain a promoter region for the yngJ gene was digested with restriction enzymes KpnI and EcoRI (both from Takara Shuzo) and purified. The DNA fragment was mixed with and ligated to the vector fragment digested with the restriction enzymes KpnI and EcoRI. The reaction mixture was used to transform *Bacillus subtilis* DB104. The transformed cells were spread on LB plates containing 1% skim milk and 10 µg/ml of kanamycin. The plates were incubated at 37° C. for 16 hours.

Primers UBF1 (SEQ ID NO:21) and SBPR1 (SEQ ID NO:22) which can be used to amplify the DNA fragment containing the promoter region were designed in order to select a clone into which the 180-bp DNA fragment was inserted from the resulting kanamycin-resistant transformants. A PCR was carried out using the combination of these two primers and TaKaRa Ex Taq (Takara Shuzo) in a reaction mixture containing 1 mM PMSF as follows: 20 cycles of 94° C. for 30 seconds, 55° C. for 1 minute, and 72° C. for 1 minute.

Thus, a clone into which the 180-bp DNA fragment was inserted was selected. A plasmid was prepared from the selected transformant and designated as pND20.

The other 22 DNA fragments were subjected to similar procedures. Then, 18 clones in which the promoter sequences were different from that in pN20 were obtained among clones for which transformants were obtained. A total of 19 types of plasmids were prepared from the transformants.

Example 4

Production of Hyperthermostable Protease Using Stationary Phase-Specific Expression Vectors (1) Cultivation of *Bacillus subtilis* cells transformed with plasmids containing hyperthermostable protease PFUS gene and preparation of crude enzyme solutions

*Bacillus subtilis* DB104/pND20 is a strain made by introducing, into *Bacillus subtilis* DB104, the plasmid pND20 which was prepared in Example 3 and contains the hyperthermostable protease PFUS gene. *Bacillus subtilis* DB104/pND20 was cultured in 1 ml of TKRBS1 medium (20 mg/ml of Polypeptone, 2 mg/ml of yeast extract, 10 mg/ml of meat extract, 40 mg/ml of glucose, 20 µg/ml of $FeSO_4$ $7H_2O$, 20 µg/ml of $MnSO_4.5H_2O$, and 2 µg/ml of $ZnSO_4.7H_2O$) containing 10 µg/ml of kanamycin at 37° C. 100 µl of the culture was collected 4, 7, 10 or 13 days after the initiation of cultivation. The culture was heated at 95° C. for 30 minutes, and then centrifuged to collect a supernatant. The supernatant was used as a crude enzyme solution.

Crude enzyme solutions were prepared in a similar manner using *Bacillus subtilis* DB104 harboring one of the other 18 plasmids.

(2) Comparison of abilities to produce hyperthermostable protease

Activities of the hyperthermostable protease PFUS were determined by spectroscopically measuring p-nitroaniline generated by a hydrolysis reaction with the enzyme using Suc-Ala-Ala-Pro-Phe-p-NA (Sigma) as a substrate.

Specifically, an enzyme preparation for which the enzymatic activity was to be determined was appropriately diluted with 100 mM phosphate buffer (pH 7.0). 50 µl of a solution containing Suc-Ala-Ala-Pro-Phe-p-NA at a concentration of 1 mM in 100 mM phosphate buffer (pH 7.0) was added to 50 µl of the sample solution. The mixture was reacted at 95° C. for 30 minutes. The reaction mixture was then cooled on ice to stop the reaction. Absorbance at 405 nm was measured to determined the amount of generated p-nitroaniline.

One unit of the enzyme was defined as the amount of the enzyme that generates 1 μmol of p-nitroaniline at 95° C. in 1 minute.

The amount of the expressed enzyme protein was calculated on the basis of the determined enzymatic activity assuming that the specific activity of the hyperthermostable protease PFUS is 9.5 units/mg protein.

Hyperthermostable protease activities were determined using the crude enzyme solutions prepared in Example 4-(1) as enzyme preparations. As a result, expression of the hyperthermostable protease PFUS was observed using six of the plasmids (pND1, pND6, pND10, pND19, pND20, pND23). Nucleotide sequences of the promoter regions incorporated into these six plasmids are shown in SEQ ID NOS:1 to 6. Expression levels observed using these six plasmids are shown in Table 3. In Table 3, the results are expressed as relative values defining the expression level observed using *Bacillus subtilis* DB104/pSPO124ΔC as 1.

TABLE 3

| Plasmid | Cultivation time (day) | | | |
|---|---|---|---|---|
| | 4 | 7 | 10 | 13 |
| pND1 | 0.10 | 0.21 | 0.28 | 0.29 |
| pND6 | 0.01 | 0.79 | 1.18 | 0.86 |
| pND10 | 1.51 | 1.53 | 1.64 | 1.04 |
| pND19 | 0.80 | 0.60 | 0.61 | 0.52 |
| pND20 | 1.93 | 2.45 | 2.17 | 2.00 |
| pND23 | 0.98 | 0.98 | 1.01 | 0.95 |

As seen from Table 3, increases in expression levels of the hyperthermostable protease PFUS were observed using pND6 (about 1.2-fold), pND10 (about 1.5-fold or more), and pND20 (about 2-fold or more) as compared with the expression level observed using pSPO124ΔC. Using pND6, almost no expression of the hyperthermostable protease PFUS was observed on day 4 in the early stage of cultivation. The expression level was greater than that observed using pSPO124ΔC on day 10 in the later stage of cultivation.

For plasmids with which expression of the hyperthermostable protease PFUS was observed, cultivation periods in days which resulted in the maximal expression levels of the hyperthermostable protease PFUS, and the productivities are shown in Table 4 along with the names of the genes from which the promoters originated. The productivity in Table 4 is expressed as the amount in mg per liter of culture.

TABLE 4

| Plasmid | Gene from which promoter originated | Productivity (mg) | Cultivation period (day) |
|---|---|---|---|
| pSPO124ΔC | aprE | 342 | 13 |
| pND1 | acoA | 92.9 | 13 |
| pND6 | spoIIB | 310 | 10 |
| pND10 | ybcO | 514 | 10 |
| pND19 | yjdB | 243 | 10 |
| pND20 | yngJ | 526 | 7 |
| pND23 | yrzE | 279 | 10 |

As seen from Table 4, a greater amount of the hyperthermostable protease PFUS was produced using pND6, pND10 and pND20 in shorter a cultivation period (in days) as compared with the results for pSPO124ΔC.

Example 5

Production of Alkaline Protease, Nitrophenylphosphatase, Pyrrolidone Carboxyl Peptidase and Methionyl Aminopeptidase Using Stationary Phase-Specific Expression Vectors (1) Preparation of Vectors A region excluding the protease PFUS gene as a reporter gene, i.e., a region containing the promoter region, the SD sequence, the secretion signal and the vector was amplified by a PCR. In the PCR, primers NDF1 (SEQ ID NO:23) and NDR1 (SEQ ID NO:24) as well as one of the plasmids pND1, pND6, pND10, pND19 and pND23 which were constructed in Example 3 above, or pSPO124ΔC (control), as a template were used. The amplified fragments were digested with restriction enzymes SpeI and MluI (both from Takara Shuzo) and purified. These fragments were used as vector fragments below.

(2) Preparation of Reporter Genes and Construction of Expression Vectors (i) Alkaline Protease Gene A plasmid A2GR7310 which contains an alkaline protease gene from a hyperthermophile *Aeropyrum pernix* K1 was obtained from National Institute of Technology and Evaluation. A region encoding alkaline protease was amplified by a PCR using the plasmid as a template as well as primers AP1F1 (SEQ ID NO:25) and AP1R1 (SEQ ID NO:26). The amplified fragment was digested with restriction enzymes SpeI and MluI (both from Takara Shuzo) and purified. This fragment was used as a reporter gene fragment below.

The nucleotide sequence of the alkaline protease gene from *A. pernix* which was used as a reporter gene is shown in SEQ ID NO:33.

Recombinant plasmids (expression vectors) obtained by ligating the reporter gene fragment to the vector fragments derived from pND6, pND10 and pSPO124ΔC were designated as pND6A1, pND10A1 and pSPOA1, respectively.

(ii) Nitrophenylphosphatase Gene

A plasmid A2GR0030 which contains a nitrophenylphosphatase gene from a hyperthermophile *Aeropyrum pernix* K1 was obtained from National Institute of Technology and Evaluation. A region encoding nitrophenylphosphatase was amplified by a PCR using the plasmid as a template as well as primers AP7F1 (SEQ ID NO:27) and AP7R1 (SEQ ID NO:28). The amplified fragment was digested with restriction enzymes SpeI and MluI (both from Takara Shuzo) and purified. This fragment was used as a reporter gene fragment below.

The nucleotide sequence of the nitrophenylphosphatase gene from *A. pernix* which was used as a reporter gene is shown in SEQ ID NO:34.

Recombinant plasmids (expression vectors) obtained by ligating the reporter gene fragment to the vector fragments derived from pND10, pND23 and pSPO124ΔC were designated as pND10A7, pND23A7 and pSPOA7, respectively.

(iii) Pyrrolidone Carboxyl Peptidase Gene

A plasmid 2708 which contains a pyrrolidone carboxyl peptidase gene from a hyperthermophile *Pyrococcus horikoshii* OT3 was obtained from National Institute of Technology and Evaluation. A region encoding pyrrolidone carboxyl peptidase was amplified by a PCR using the plasmid as a template as well as primers PH1F1 (SEQ ID NO:29) and PH1R1 (SEQ ID NO:30). The amplified fragment was digested with restriction enzymes SpeI and MluI (both from Takara Shuzo) and purified. This fragment was used as a reporter gene fragment below.

The nucleotide sequence of the pyrrolidone carboxyl peptidase gene from *P. horikoshii* which was used as a reporter gene is shown in SEQ ID NO:35.

Recombinant plasmids (expression vectors) obtained by ligating the reporter gene fragment to the vector fragments derived from pND10, pND19 and pSPO124ΔC were designated as pND10P1, pND19P1 and pSPOP1, respectively.

(iv) Methionyl Aminopeptidase Gene

A PCR-amplified fragment PHO628PCR for a methionyl aminopeptidase gene from a hyperthermophile *Pyrococcus horikoshii* OT3 was obtained from National Institute of Technology and Evaluation. A region encoding methionyl aminopeptidase was amplified by a PCR using the fragment as a template as well as primers PH2F1 (SEQ ID NO:31) and PH2R1 (SEQ ID NO:32). The amplified fragment was digested with restriction enzymes SpeI and MluI (both from Takara Shuzo) and purified. This fragment was used as a reporter gene fragment below.

The nucleotide sequence of the methionyl aminopeptidase gene from *P. horikoshii* which was used as a reporter gene is shown in SEQ ID NO:36.

Recombinant plasmids (expression vectors) obtained by ligating the reporter gene fragment to the vector fragments derived from pND1, pND19 and pSPO124ΔC were designated as pND1P2, pND19P2 and pSPOP2, respectively.

(3) Preparation of Transformants and Expression of Reporter Genes

The respective expression vectors constructed in Example 5-(2) were used to transform *Bacillus subtilis* DB104. The transformed cells were spread on LB plates containing 1% skim milk and 10 μg/ml of kanamycin. The plates were incubated at 37° C. for 16 hours.

A clone into which one of the genes encoding the enzymes was inserted was selected from the resulting kanamycin-resistant transformants, and cultured in 1 ml of TKRBS1 medium containing 10 g/ml of kanamycin at 37° C. A culture collected after 10 days of cultivation (7 days only in case of alkaline protease) was heated at 95° C. for 30 minutes, and centrifuged to collect a supernatant. The supernatant was used as a crude enzyme solution (enzyme preparation).

(4) Measurements of Activities (i) Alkaline Protease

Alkaline protease activities were measured using gelatin (Nacalai Tesque) as a substrate as follows.

An enzyme preparation for which the enzymatic activity was to be determined was appropriately diluted with 50 mM sodium phosphate buffer (pH 7.0). The dilution was mixed with an SDS-PAGE loading buffer. The mixture was allowed to stand at room temperature for 30 minutes or longer, and then subjected to electrophoresis on 10% polyacrylamide gel containing SDS and 0.05% gelatin. After electrophoresis, the gel was washed in 50 mM sodium phosphate buffer (pH 7.0). The washed gel was incubated in 50 mM sodium phosphate buffer (pH 7.0) at 95° C. for 3 hours. The reaction mixture was then cooled on ice to stop the reaction. The gel was stained with Coomassie Blue. The gel image was converted to an image file using an image analysis software Adobe Photoshop (Adobe) and active signals were numerically expressed using NIH image software.

(ii) Nitrophenylphosphatase

Nitrophenylphosphatase activities were measured using p-nitrophenylphosphate (Sigma) as a substrate as follows.

An enzyme preparation for which the enzymatic activity was to be determined was appropriately diluted with 100 mM Tris-HCl buffer (pH 7.5) containing 1 mM $ZnCl_2$. 50 μl of a solution containing p-nitrophenylphosphate at a concentration of 2 mM in 100 mM Tris-HCl buffer (pH 7.5) containing 1 mM $ZnCl_2$ was added to 50 Al of the sample solution. The mixture was reacted at 95° C. for 10 minutes. The reaction mixture was then cooled on ice to stop the reaction. The amount of generated free phosphate was determined by measuring fluorescence emission at 590 nm due to excitation at 544 nm using Piper Phosphate Assay Kit (Molecular Probe).

(iii) Pyrrolidone Carboxyl Peptidase

Pyrrolidone carboxyl peptidase activities were measured using pyroglutamic acid 4-methyl-coumaryl-7-amide (hereinafter referred to as Pyr-MCA; Peptide Institute) as a substrate as follows.

An enzyme preparation for which the enzymatic activity was to be determined was appropriately diluted with 50 mM phosphate buffer (pH 7.0) containing 10 mM DTT and 1 mM EDTA. 50 μl of a solution containing Pyr-MCA at a concentration of 0.2 mM in 50 mM phosphate buffer (pH 7.0) containing 10 mM DTT and 1 mM EDTA was added to 50 μl of the sample solution. The mixture was reacted at 95° C. for 30 minutes. The reaction mixture was then cooled on ice to stop the reaction. The amount of generated MCA was determined by measuring fluorescence emission at 460 nm due to excitation at 355 nm.

One unit of the enzyme was defined as the amount of the enzyme that generates 1 μmol of MCA at 95° C. in one minute.

(iv) Methionyl Aminopeptidase

Methionyl aminopeptidase activities were measured using Met-Ala-Ser (Bachem) as a substrate as follows.

An enzyme preparation for which the enzymatic activity was to be determined was appropriately diluted with 100 mM potassium phosphate buffer (pH 7.5) containing 0.5 mM $CoCl_2$. 45 μl of a solution containing Met-Ala-Ser at a concentration of 1 mM in 100 mM potassium phosphate buffer (pH 7.5) containing 0.5 mM $CoCl_2$ was added to 5 μl of the sample solution. The mixture was reacted at 75° C. for 5 minutes. The reaction mixture was then cooled on ice and 10 μl of 100 mM EDTA was added thereto to stop the reaction. 50 μl of a mixture A (100 mM potassium phosphate buffer (pH 7.5) containing 0.18 mg/ml of L-amino acid oxidase, 50 μg/ml of peroxidase and 0.18 mg/ml of o-dianisidine) was added thereto. The mixture was reacted at 37° C. for 10 minutes. The reaction mixture was then cooled on ice to stop the reaction. Absorbance at 450 nm was measured.

(5) Comparison of Abilities of Production

The total enzymatic activities contained in the cultures were calculated on the basis of the enzymatic activities of the enzyme preparations measured as described in Example 5-(4).

The expression level observed using an expression vector having the promoter for the aprE gene (pSPOA1, pSPOA7, pSPOP1 or pSPOP2) was defined as 1. Relative expression levels for the respective expression vectors are shown in Table 5.

TABLE 5

| Reporter gene | Vector | Promoter | Relative expression level |
|---|---|---|---|
| *A. pernix* alkaline protease | pND6A1 | spoIIB | 6.16 |
| | pND10A1 | ybcO | 23.8 |
| | pSPOA1 | aprE | 1.00 |
| *A. pernix* nitrophenylphosphatase | pND10A7 | ybcO | 2.29 |
| | pND23A7 | yrzE | 1.68 |
| | pSPOA7 | aprE | 1.00 |

TABLE 5-continued

| Reporter gene | Vector | Promoter | Relative expression level |
|---|---|---|---|
| P. horikoshii pyrrolidone carboxyl peptidase | pND10P1 | ybcO | 1.43 |
| | pND19P1 | yjdB | 3.73 |
| | pSPOP1 | aprE | 1.00 |
| P. horikoshii methionyl aminopeptidase | pND1P2 | acoA | 1.81 |
| | pND19P2 | yjdB | 1.98 |
| | pSPOP2 | aprE | 1.00 |

INDUSTRIAL APPLICABILITY

The present invention provides a promoter that enables expression of a gene at a high level in a stationary phase-specific manner without inducing the expression of the gene.

Sequence Listing Free Text

SEQ ID NO:1; Promoter region on pND1.
SEQ ID NO:2; Promoter region on pND6.
SEQ ID NO:3; Promoter region on pND10.
SEQ ID NO:4; Promoter region on pND19.
SEQ ID NO:5; Promoter region on pND20.
SEQ ID NO:6; Promoter region on pND23.
SEQ ID NO:7; Primer aAF1 for amplifying promoter sequence of acoA gene.
SEQ ID NO:8; Primer aAR1 for amplifying promoter sequence of acoA gene.
SEQ ID NO:9; Primer spBF1 for amplifying promoter sequence of spoIIB gene.
SEQ ID NO:10; Primer spBR1 for amplifying promoter sequence of spoIIB gene.
SEQ ID NO:11; Primer ybOF1 for amplifying promoter sequence of ybcO gene.
SEQ ID NO:12; Primer ybOR1 for amplifying promoter sequence of ybco gene.
SEQ ID NO:13; Primer yjBF1 for amplifying promoter sequence of yjdB gene.
SEQ ID NO:14; Primer yjBR1 for amplifying promoter sequence of yjdB gene.
SEQ ID NO:15; Primer ynJF1 for amplifying promoter sequence of yngJ gene.
SEQ ID NO:16; Primer ynJR1 for amplifying promoter sequence of yngJ gene.
SEQ ID NO:17; Primer yrEF1 for amplifying promoter sequence of yrzE gene.
SEQ ID NO:18; Primer yrER1 for amplifying promoter sequence of yrzE gene.
SEQ ID NO:19; Primer PLF1.
SEQ ID NO:20; Primer PLR1.
SEQ ID NO:21; Primer UBF1.
SEQ ID NO:22; Primer SBPR1.
SEQ ID NO:23; Primer NDF1.
SEQ ID NO:24; Primer NDR1.
SEQ ID NO:25; Primer AP1F1 for amplifying coding region of alkaline protease gene.
SEQ ID NO:26; Primer AP1R1 for amplifying coding region of alkaline protease gene.
SEQ ID NO:27; Primer AP7F1 for amplifying coding region of nitrophenyl phosphatase gene.
SEQ ID NO:28; Primer AP7R1 for amplifying coding region of nitrophenyl phosphatase gene.
SEQ ID NO:29; Primer PH1F1 for amplifying coding region of pyrrolidone-carboxyl peptidase gene.
SEQ ID NO:30; Primer PH1R1 for amplifying coding region of pyrrolidone-carboxyl peptidase gene.
SEQ ID NO:31; Primer PH2F1 for amplifying coding region of methionyl aminopeptidase gene.
SEQ ID NO:32; Primer PH2R1 for amplifying coding region of methionyl aminopeptidase gene.

The invention claimed is:

1. An isolated DNA consisting of a nucleotide sequence of any one of SEQ ID NO:1, SEQ ID NO:2, SEQ ID NO:4, SEQ ID NO:5, and SEQ ID NO:6 which exhibits a promoter activity and expresses a nucleic acid operably linked to the promoter only during stationary phase in a Gram-positive bacterium.

2. An expression vector, comprising the isolated DNA of claim 1 and an exogenous gene, wherein the vector expresses the exogenous gene in a stationary phase-specific manner.

3. The expression vector of claim 2, wherein the vector is selected from the group consisting of a plasmid vector, a phage vector and a virus vector.

4. A host cell transformed with the expression vector of claim 2.

5. A kit for producing a protein which contains the DNA of claim 1.

6. A kit for producing a protein which contains the expression vector of claim 2.

7. A method for producing a protein, the method comprising:
    culturing to stationary phase a Gram-positive bacterium transformed with a recombinant DNA having a nucleic acid encoding a protein operably linked to a nucleotide sequence selected from the group consisting of SEQ ID NO:1, SEQ ID NO:2, SEQ ID NO:4, SEQ ID NO:5, and SEQ ID NO:6 which exhibits promoter activity, so that the nucleic acid is expressed from the promoter in said nucleotide sequence only during stationary phase in the Gram-positive bacterium; and
    collecting from the resulting culture a protein expressed from the nucleic acid.

* * * * *

SEQUENCE LISTING

```
<160> NUMBER OF SEQ ID NOS: 36

<210> SEQ ID NO 1
<211> LENGTH: 180
<212> TYPE: DNA
<213> ORGANISM: Artificial Sequence
<220> FEATURE:
<223> OTHER INFORMATION: A sequence for promoter region on pND1.

<400> SEQUENCE: 1
gtcaaaggcc gggtgatatc cggtcttttt tttgcatgct gtaaaacgag acaaatgaat      60
cagtttgaga caaaacgaga cacacgtctc aaactgtctc caaagtgaag atgagaagac     120
tgattttacg ggctcaaaag actggcacac ttcttgcatt tataatggtg aaccctaaat     180

<210> SEQ ID NO 2
<211> LENGTH: 190
<212> TYPE: DNA
<213> ORGANISM: Artificial Sequence
<220> FEATURE:
<223> OTHER INFORMATION: A sequence for promoter region on pND6.

<400> SEQUENCE: 2
ccgcagggag catttttagcc tatttatacg gtgactctat catttctttt tatatcaaaa      60
tggcattggg ctgactgctg aaaaatttga cgaacgtttt ttggacaagg cgacaaaagt     120
```

```
cttgttctttt ttttctttgc ctgtgctaaa gtgtgtagca tgaaaagccg acaagaacgg    180
tcaagcaaat                                                            190

<210> SEQ ID NO 3
<211> LENGTH: 180
<212> TYPE: DNA
<213> ORGANISM: Artificial Sequence
<220> FEATURE:
<223> OTHER INFORMATION: A sequence for promoter region on pND10.

<400> SEQUENCE: 3
ctgttttctt cgagaggata gcttgtcagc ttttctattt ttaaagggtt aaaatattct     60
atttatacta attaatgtaa tttttaggat aatatacaaa atcccccttaa cttcgacaat   120 tgcaatctgg tattatcgta tcgcatggga gctatgtcaa tagactctat gcaaaaattg   180

<210> SEQ ID NO 4
<211> LENGTH: 184
<212> TYPE: DNA
<213> ORGANISM: Artificial Sequence
<220> FEATURE:
<223> OTHER INFORMATION: A sequence for promoter region on pND19.

<400> SEQUENCE: 4
tgctattaac attttaagga tggccattct ctctcagcaa ttttccatca taaatacaaa     60
ctctgtgcag ggcacacaat attcttagct caaatcaatt gatcgttcac atattattaa   120
catttattta caaggaaaat aattactttt attgaattgt tatagtgcaa gacaaaaaac   180
ttta                                                                 184

<210> SEQ ID NO 5
<211> LENGTH: 180
<212> TYPE: DNA
<213> ORGANISM: Artificial Sequence
<220> FEATURE:
<223> OTHER INFORMATION: A sequence for promoter region on pND20.

<400> SEQUENCE: 5
ttcccggctt tatcaaaggg ccaagttatt gcgtttacga tatggatggt atgcgcctac     60
tgcatgtatt tgctcatccc gctgatatta tcacataaaa aatgattcag ttttaattt    120 cagactttc ttgtcaggga atgattatag aactcgccta ataggatgtt acaaagatgt    180

<210> SEQ ID NO 6
<211> LENGTH: 180
<212> TYPE: DNA
<213> ORGANISM: Artificial Sequence
<220> FEATURE:
<223> OTHER INFORMATION: A sequence for promoter region on pND23.

<400> SEQUENCE: 6
tgaccaatat cacaaaatac aatacgactg tgcgaaacgc aatagtgaga agctcttcca     60
ttatgcacct ccaactcatt ataggttgca acaaaatgat caatttatgt aagaaaaacc   120
gattgcattt cacaaagctt ttacgtctaa ttcatgggat aagggaatac attttttacaa  180

<210> SEQ ID NO 7
<211> LENGTH: 28
<212> TYPE: DNA
<213> ORGANISM: Artificial Sequence
<220> FEATURE:
<223> OTHER INFORMATION: A sequence of primer aAF1 for amplifying
      promoter sequence of acoA gene.
```

```
<400> SEQUENCE: 7
gggggaattc gtcaaaggcc gggtgata                                          28

<210> SEQ ID NO 8
<211> LENGTH: 28
<212> TYPE: DNA
<213> ORGANISM: Artificial Sequence
<220> FEATURE:
<223> OTHER INFORMATION: A sequence of primer aAR1 for amplifying
      promoter sequence of acoA gene.

<400> SEQUENCE: 8 gggggggtacc atttagggtt caccatta                                         28

<210> SEQ ID NO 9
<211> LENGTH: 28
<212> TYPE: DNA
<213> ORGANISM: Artificial Sequence
<220> FEATURE:
<223> OTHER INFORMATION: A sequence of primer spBF1 for amplifying
      promoter sequence of spoIIB gene.

<400> SEQUENCE: 9
gggggaattc ccgcagggag cattttag                                          28

<210> SEQ ID NO 10
<211> LENGTH: 28
<212> TYPE: DNA
<213> ORGANISM: Artificial Sequence
<220> FEATURE:
<223> OTHER INFORMATION: A sequence of primer spBR1 for amplifying
      promoter sequence of spoIIB gene.

<400> SEQUENCE: 10 gggggggtacc atttgcttga ccgttgtt                                         28

<210> SEQ ID NO 11
<211> LENGTH: 28
<212> TYPE: DNA
<213> ORGANISM: Artificial Sequence
<220> FEATURE:
<223> OTHER INFORMATION: A sequence of primer ybOF1 for amplifying
      promoter sequence of ybcO gene.

<400> SEQUENCE: 11
gggggaattc ctgtttttct cgagagga                                          28

<210> SEQ ID NO 12
<211> LENGTH: 28
<212> TYPE: DNA
<213> ORGANISM: Artificial Sequence
<220> FEATURE:
<223> OTHER INFORMATION: A sequence of primer ybOR1 for amplifying
      promoter sequence of ybcO gene.

<400> SEQUENCE: 12 gggggggtacc caattttgc atagagtc                                          28

<210> SEQ ID NO 13
<211> LENGTH: 28
<212> TYPE: DNA
<213> ORGANISM: Artificial Sequence
<220> FEATURE:
<223> OTHER INFORMATION: A sequence of primer yjBF1 for amplifying
      promoter sequence of yjdB gene.
```

```
<400> SEQUENCE: 13
gggggaattc tgctattaac attttaag                                  28

<210> SEQ ID NO 14
<211> LENGTH: 28
<212> TYPE: DNA
<213> ORGANISM: Artificial Sequence
<220> FEATURE:
<223> OTHER INFORMATION: A sequence of primer yjBR1 for amplifying
      promoter sequence of yjdB gene.

<400> SEQUENCE: 14
ggggggtacc taaagttttt tgtcttgc                                  28

<210> SEQ ID NO 15
<211> LENGTH: 28
<212> TYPE: DNA
<213> ORGANISM: Artificial Sequence
<220> FEATURE:
<223> OTHER INFORMATION: A sequence of primer ynJF1 for amplifying
      promoter sequence of yngJ gene.

<400> SEQUENCE: 15
gggggaattc ttcccggctt tatcaaag                                  28

<210> SEQ ID NO 16
<211> LENGTH: 28
<212> TYPE: DNA
<213> ORGANISM: Artificial Sequence
<220> FEATURE:
<223> OTHER INFORMATION: A sequence of primer ynJR1 for amplifying
      promoter sequence of yngJ gene.

<400> SEQUENCE: 16
ggggggtacc acatctttgt aacatcct                                  28

<210> SEQ ID NO 17
<211> LENGTH: 28
<212> TYPE: DNA
<213> ORGANISM: Artificial Sequence
<220> FEATURE:
<223> OTHER INFORMATION: A sequence of primer yrEF1 for amplifying
      promoter sequence of yrzE gene.

<400> SEQUENCE: 17
gggggaattc tgaccaatat cacaaaat                                  28

<210> SEQ ID NO 18
<211> LENGTH: 28
<212> TYPE: DNA
<213> ORGANISM: Artificial Sequence
<220> FEATURE:
<223> OTHER INFORMATION: A sequence of primer yrER1 for amplifying
      promoter sequence of yrzE gene.

<400> SEQUENCE: 18
ggggggtacc ttgtaaaaat gtattccc                                  28

<210> SEQ ID NO 19
<211> LENGTH: 30
<212> TYPE: DNA
<213> ORGANISM: Artificial Sequence
<220> FEATURE:
<223> OTHER INFORMATION: A sequence of primer PLF1.

<400> SEQUENCE: 19
```

-continued

```
ggggggtacc caaaaggaga gggggatccg                                    30

<210> SEQ ID NO 20
<211> LENGTH: 29
<212> TYPE: DNA
<213> ORGANISM: Artificial Sequence
<220> FEATURE:
<223> OTHER INFORMATION: A sequence of primer PLR1.

<400> SEQUENCE: 20
gggggaattc ttaggaacgt acagacggc                                     29

<210> SEQ ID NO 21
<211> LENGTH: 20
<212> TYPE: DNA
<213> ORGANISM: Artificial Sequence
<220> FEATURE:
<223> OTHER INFORMATION: A sequence of primer UBF1.

<400> SEQUENCE: 21
aaaggctttt aagccgtctg                                               20

<210> SEQ ID NO 22
<211> LENGTH: 20
<212> TYPE: DNA
<213> ORGANISM: Artificial Sequence
<220> FEATURE:
<223> OTHER INFORMATION: A sequence of primer SBPR1.

<400> SEQUENCE: 22
cctgcgcaga catgttgctg                                               20

<210> SEQ ID NO 23
<211> LENGTH: 29
<212> TYPE: DNA
<213> ORGANISM: Artificial Sequence
<220> FEATURE:
<223> OTHER INFORMATION: A sequence of primer NDF1.

<400> SEQUENCE: 23
ggtgacgcgt aagctttaat gcggtagtt                                     29

<210> SEQ ID NO 24
<211> LENGTH: 29
<212> TYPE: DNA
<213> ORGANISM: Artificial Sequence
<220> FEATURE:
<223> OTHER INFORMATION: A sequence of primer NDR1.

<400> SEQUENCE: 24
ggggactagt cctccggcag cctgcgcag                                     29

<210> SEQ ID NO 25
<211> LENGTH: 28
<212> TYPE: DNA
<213> ORGANISM: Artificial Sequence
<220> FEATURE:
<223> OTHER INFORMATION: A sequence of primer AP1F1 for amplifying
      coding region of alkaline protease gene.

<400> SEQUENCE: 25
gaggactagt ggtcgctgta gtaactgg                                      28

<210> SEQ ID NO 26
<211> LENGTH: 28
<212> TYPE: DNA
```

```
<213> ORGANISM: Artificial Sequence
<220> FEATURE:
<223> OTHER INFORMATION: A sequence of primer AP1R1 for amplifying
      coding region of alkaline protease gene.

<400> SEQUENCE: 26
ggggacgcgt cagcttgaga cggcagtc                                        28

<210> SEQ ID NO 27
<211> LENGTH: 35
<212> TYPE: DNA
<213> ORGANISM: Artificial Sequence
<220> FEATURE:
<223> OTHER INFORMATION: A sequence of primer AP7F1 for amplifying
      coding region of nitrophenyl phosphatase gene.

<400> SEQUENCE: 27
gaggactagt gtttgcggat ctagacggcg tgata                                35

<210> SEQ ID NO 28
<211> LENGTH: 35
<212> TYPE: DNA
<213> ORGANISM: Artificial Sequence
<220> FEATURE:
<223> OTHER INFORMATION: A sequence of primer AP7R1 for amplifying
      coding region of nitrophenyl phosphatase gene.

<400> SEQUENCE: 28
ggggacgcgt caccccctc tgcagaactc gctga                                 35

<210> SEQ ID NO 29
<211> LENGTH: 28
<212> TYPE: DNA
<213> ORGANISM: Artificial Sequence
<220> FEATURE:
<223> OTHER INFORMATION: A sequence of primer PH1F1 for amplifying
      coding region of pyrrolidone-carboxyl peptidase gene.

<400> SEQUENCE: 29
gaggactagt gaagatctta ttgactgg                                        28

<210> SEQ ID NO 30
<211> LENGTH: 30
<212> TYPE: DNA
<213> ORGANISM: Artificial Sequence
<220> FEATURE:
<223> OTHER INFORMATION: A sequence of primer PH1R1 for amplifying
      coding region of pyrrolidone-carboxyl peptidase gene.

<400> SEQUENCE: 30
ggggacgcgt cacctgagtt gtgatgaatg                                      30

<210> SEQ ID NO 31
<211> LENGTH: 30
<212> TYPE: DNA
<213> ORGANISM: Artificial Sequence
<220> FEATURE:
<223> OTHER INFORMATION: A sequence of primer PH2F1 for amplifying
      coding region of methionyl aminopeptidase gene.

<400> SEQUENCE: 31
gaggactagt ggatgttgac aagcttattg                                      30

<210> SEQ ID NO 32
<211> LENGTH: 30
<212> TYPE: DNA
<213> ORGANISM: Artificial Sequence
```

```
<220> FEATURE:
<223> OTHER INFORMATION: A sequence of primer PH2R1 for amplifying
      coding region of methionyl aminopeptidase gene.

<400> SEQUENCE: 32
ggggacgcgt cattccgttg ttacagtcac                                      30

<210> SEQ ID NO 33
<211> LENGTH: 1323
<212> TYPE: DNA
<213> ORGANISM: Aeropyrum pernix

<400> SEQUENCE: 33
gtggtcgctg tagtaactgg tgtaattcag gtgggaacta agatcgcggc tattgcgatc     60
gcgctgatct tcattctgcc tctcttccct gtttatacgg gatcggcggc tggggctagc    120
acggttgtga tagctaagat taatcctgag gagtttaacc ctaaggcggt ggaggctctt    180
cagggcaagg taatatatgt tgctgatctg gcccccgttg ctataattag cataccagga    240
aaggctgtag gcctgctctc taaactacct ggtgttgtca gcgtttccga ggacggcgtg    300
gtccaggcta tggccaagcc gccgtgggct ggcggcggga ataagtctca gcctgccgag    360
gtcctgcctt ggggtgtcga ctatatcgat gccgagctag tatggcccga tggggttacc    420
ggctgggtta cgttaacgg tgacgggggаc ggcgagatag aggttgccgt tattgacact     480
ggtgtcgata aggaccatcc cgaccttgca ggcaacattg tctgggggat atctgttttg    540
aacggcagga tatcctccaa ctaccaggat agaaacggcc acggtacaca cgtaacgggc    600
actgtagccg ccatagacaa cgatataggg gtgataggggg ttgcacacag cgtggagatc    660
tacgccgtta agctctcgg taacgggggt tacggcagct ggagcgacct tataatagct    720
atagaccttg ctgtgaaggg gccggacggc gtaattgacg ctgatggaga tggcgtcgtc    780
gctggggatc cagacgatga tgctccagag gttatctcca tgagcctagg tgggagcagc    840
ccaccaccag aactccacga cgttatcaag gcggcgtaca accttggaat aactattgtc    900
gcagcagcgg gtaacgacgg ggcggacagc ccctcatacc ctgcagccta ccctgaggta    960
atagcggtag gcgctataga cgagaacggc aacgtaccta gctggagcaa tagaaaccct   1020
gaggttgctg cacctggagt gaacatacta agcacctacc ccgacgatac ctatgaggag   1080
ctgagcggca ctagcatggc gactccacac gtgtcaggga ctgtggctct aatacaggct   1140
gccaggctgg ccgctggcct ccctctactc cctccgggaa gcgagagtga cactactcca   1200
gacaccgtga gggcgtact gcatactact gctactgacg cggggagaccc aggctacgat   1260 agcctgtatg gatacggtat catagacgcc tatgacgccg tgcagactgc cgtctcaagc   1320
tga                                                                 1323

<210> SEQ ID NO 34
<211> LENGTH: 768
<212> TYPE: DNA
<213> ORGANISM: Aeropyrum pernix

<400> SEQUENCE: 34
gtgtttgcgg atctagacgg cgtgatatgg cttgggcagg aacctataga ggataaccta     60
gtagtgctta ggactctggc gagcgagggt aggcttgtgg ttctcactaa taattcgacg    120
cgaagtagga gagtttacgc ggctatgctc gagagggtgg gcctcgacat agagcccggg    180
aggatagtaa cgagcgccta cagcgccgcc gtcctgctga agaaaaagct gggaccatcc    240
accgccctgg ttgtagggga ggagggggctg gttgaagagc ttgctgtgga gggccatgta    300
```

```
gtggcgagct cgagcgacaa catcgacgtt gatgcggtgg tcgtcggcct cgacaggaac    360
ctcacctatg ggaagctggc gagggctgcc tccgcaatac acagcgggag ccttttcgtg    420
gcgacgaacc tcgaccacgc cctaccaacc cccagaggcc tcataccagg tgcaggatcc    480
attgtggctc ttctggagaa ggcaacgggg gtcaagcctg cgattgtcgc tgggaagccg    540
tccaggggct tggccgaggt tctagagagc cttttcaagc cggtcaggcc cctcgtggtg    600
ggtgatagga tagatactga cgtggagttc gccagggcct ggggtgttga ttctcttctc    660
gtgctcactg gcctctacag gggtgtcagc atagaggagg cttctaggaa ggctggggag    720
ggggtgaggg ttgccaggag tctcagcgag ttctgcagag gggggtag                 768

<210> SEQ ID NO 35
<211> LENGTH: 621
<212> TYPE: DNA
<213> ORGANISM: Pyrococcus horikoshii

<400> SEQUENCE: 35
atgaagatct tattgactgg ctttgagccc tttggaggtg acgataagaa tcccactatg     60
gatatagttg aagctctaag cgaaaggata cctgaggtcg ttggggagat actaccgcgta   120 tccttcaaga gggctagaga aaagctcctc aaggtacttg acgatgttag ccagatata    180 accataaacc tgggcttggc cccaggaaga acgcacatat ccgttgagag agtagccgtg    240
aacatgatag atgcgaggat tccggataat gatggagagc aaccgaagga tgaacccata    300
gtcgagggag gacctgcagc ttatttttgca acaatacccca ctaggagat agtcgaagag   360 atgaagaaga acggcattcc agcggttctc tcttacacgg ctggaactta tctctgcaat    420
ttcgccatgt atttaacctt acacacatca gctaccaagg gatatcccaa gattgctggc    480
ttcatacacg ttccctacac tccggatcaa gtcctggaga aaagaatac tccgagcatg    540 tctctagatt tagaaataaa gggagtggag atagcaataa gggttgctca gagcgcgcta    600
cattcatcac aactcaggta g                                              621

<210> SEQ ID NO 36
<211> LENGTH: 888
<212> TYPE: DNA
<213> ORGANISM: Pyrococcus horikoshii

<400> SEQUENCE: 36
atggatgttg acaagcttat tgaagccggt aaaatagcta aaaaggttag agaagaagcc     60
gttaaacttg caaagccagg agtttcgctc ttggaactgg cagagaaaat tgagagtaga   120
atagttgaac ttggaggtaa gccagctttt ccggcaaacc tttccctaaa tgaggtcgct    180
gcccactaca ctccttacaa gggagatcaa actgttctca agagggaga ctatctaaag    240 atagatttgg gagttcatat agatggatac atagctgata ctgctgtaac cgttagggtt    300
ggaatggatt ttgatgaact tatggaagct gctaaagaag ccctggaaag cgcaatttca    360
gttgcaaggg ccggtgtcga agttaaagaa ctcgggaaag caatagaaaa tgaaattagg    420
aagagaggct ttaaccccat tgtaaacctt agtgggcata aaatagagag gtacaagctt    480
catgctgggg taagcatccc caatatctac agacccacg ataactatgt cctccaggaa    540
ggagatgtct ttgcaataga acccttgca acaacgggtg cggggcaagt tatagaagtt    600 cccccccacgt taatatacat gtacgtcagg gatgcccccag tcaggatggc ccaagccagg    660
tttctgcttg ctaagataaa gagggagtac aagacacttc cctttgctta taggtggttg    720
```

```
                                       -continued caaggagaga  tgcccgaagg  gcagttaaaa  ctagccttaa  gatccctgga  gagatccggg      780
gccttgtacg  gttaccctgt  gctaagggag  ataagggggag gaatggtcac  gcagttcgag      840
catacaataa  tagttgaaaa  agactccgtg  actgtaacaa  cggaatga                    888
```